United States Patent [19]

Albrecht et al.

[11] 4,441,919

[45] Apr. 10, 1984

[54] HERBICIDAL COMPOSITIONS

[75] Inventors: Konrad Albrecht, Kelkheim; Heinz Frensch, Frankfurt am Main; Hans Schumacher, Flörsheim am Main, all of Fed. Rep. of Germany

[73] Assignee: Hoechst Aktiengesellschaft, Frankfurt am Main, Fed. Rep. of Germany

[21] Appl. No.: 341,751

[22] Filed: Jan. 22, 1982

Related U.S. Application Data

[63] Continuation of Ser. No. 138,885, Apr. 10, 1980, abandoned.

[30] Foreign Application Priority Data

Apr. 12, 1979 [DE] Fed. Rep. of Germany ....... 2914867

[51] Int. Cl.$^3$ ............................................. A01N 37/36
[52] U.S. Cl. .................................. 71/120; 71/DIG. 1; 260/208
[58] Field of Search ........................... 71/120, DIG. 1; 260/208

[56] References Cited

U.S. PATENT DOCUMENTS

| | | | |
|---|---|---|---|
| 3,056,642 | 10/1962 | Kesler et al. ........................ | 260/208 |
| 3,083,089 | 3/1963 | Renner ........................... | 71/DIG. 1 |
| 3,251,674 | 5/1966 | Kido ........................................ | 71/120 |
| 3,385,690 | 5/1968 | Luckenbaugh ........................ | 71/120 |
| 3,948,636 | 4/1976 | Marks ............................. | 71/DIG. 1 |
| 4,129,435 | 12/1978 | Takematsu et al. .................. | 71/120 |
| 4,163,662 | 8/1979 | Baker, Jr. ........................ | 71/DIG. 1 |

FOREIGN PATENT DOCUMENTS

| | | | |
|---|---|---|---|
| 680087 | 2/1964 | Canada ........................... | 71/DIG. 1 |
| 287463 | 12/1968 | U.S.S.R. ......................... | 71/DIG. 1 |

OTHER PUBLICATIONS

Color Index, (1971), Soc. of Dyers–3rd Ed. 4, pp. 4227–4228, (1971).

*Primary Examiner*—Glennon H. Hollrah
*Attorney, Agent, or Firm*—Curtis, Morris & Safford

[57] ABSTRACT

Liquid, herbicidal compositions containing Linuron as active substance in the form of emulsifiable concentrates or of aqueous suspension concentrates contain as crystallization inhibiting substance 0.05 to 2% by weight of fat-soluble disazo dyes which prevent the active substance from crystallizing in the aqueous emulsions of the emulsifiable concentrates and in the aqueous suspension concentrates and the aqueous dilutions thereof.

9 Claims, No Drawings

HERBICIDAL COMPOSITIONS

This is a continuation, of application Ser. No. 138,885 filed Apr. 10, 1980, now abandoned.

This invention relates to liquid, herbicidal compositions in the form of emulsifiable concentrates or aqueous suspension concentrates containing as active ingredient 3-(3,4-dichloro-phenyl)-1-methyl-1-methoxy-urea (common name Linuron), the usual formulation auxiliaries and additionally fat-soluble disazo dyes as crystallization inhibiting constituent preventing the active ingredient from crystallizing in the aqueous emulsions of the concentrates and in the aqueous suspension concentrates and the aqueous dilutions thereof.

It is known to use Linuron as herbicide (cf. German Pat. No. 1,028,986). The active ingredient is mostly applied in the form of suspensions in water obtained by stirring a wettable powder of Linuron with water. To prepare aqueous suspensions the wettable powder has to be weighed exactly. In practice, weighing in the field is rather complicated and often not exact, especially if it is windy. Powder dusts and can be blown off and the users are directly exposed to this dust. The manufacture of wettable powders containing Linuron is complicated as well. Because of the low melting point of the active substance of 93° to 94° C. and its soft and non brittle consistency, expensive, fine and adsorbent carrier materials such as synthetic silicic acid must be used for formulation in order to prevent the milled product from sintering in high power mills such as blower or pin mills as well as air jet mills as a result of the heat generated in the milling process. In spite of this necessary expenditure, the suspension properties of wettable powders containing Linuron hardly meet the international standards of the WHO and CIPAC regulations although the wettable powder particles have a high fineness with average particle sizes in the range of from 5 to 20 microns, with at most 2% by weight having sizes above 44 microns.

It is, therefore, highly desirable to apply Linuron in the form of a liquid, pourable concentrate, for example as an aqueous suspension concentrate yielding a fine dispersion or an emulsifiable concentrate yielding an emulsion. Liquid dispersion concentrates and emulsifiable concentrates are easier to handle and can be dosed more readily than wettable powder formulations. Moreover, their manufacture is simpler.

Emulsifiable concentrates are solutions of active substances in suitable solvents together with appropriate emulsifiers which ensure that stable emulsions are formed when the emulsifiable concentrate is diluted with water. Emulsifiable concentrates are produced, for example, in agitation vessels.

Linuron is very soluble in aromatic solvents as normally used for the manufacture of emulsifiable concentrates. Usual emulsifier mixtures yield emulsifiable concentrates with such Linuron solutions.

When emulsifiable Linuron concentrates of this type, for example as described in GB-PS No. 982,344, are stirred with water, first an emulsion is formed which soon changes into a so-called suspo-emulsion, i.e. an aqueous dispersion which contains side by side solid particles of active substance and fine droplets of active substance solution in water-insoluble solvents, from which Linuron crystals are formed quite rapidly and precipitate and deposit in the form of needles having a length of 100 to 250 microns. Spray liquors from such emulsions or suspo-emulsions are, above all, less effective than spray liquors or aqueous wettable powder suspensions of comparable concentration since, due to crystallization, the Linuron is distributed and hence applied in the form of coarser particles and less homogeneously.

The emulsifiable Linuron concentrates described in Japanese Patent Specification No. Sho 4,510,359 (application No. Sho 42-13123) also form spontaneously Linuron crystals when being stirred into water, which crystals grow to a length of up to 250 microns within a few minutes, so that a reliable biological effect is no longer ensured and nozzles and protecting filters of spraying devices can be clogged. This crystallization is promoted by stirring of the spray emulsion.

Suspension concentrates are concentrated aqueous suspensions of finely ground solid active substance which are slightly soluble in water and which should have a melting point above 50° C. For their manufacture the still coarse suspension of active substance containing the necessary formulation auxiliaries is pumped into a so-called friction or sand mill through a flowing bed of small glass, quartz or corundum beads rotating in a steel cylinder by means of a stirring shaft. In this process dust cannot occur and, therefore, expensive dust filter units are not required. The suspension is milled while cooling with water.

Aqueous suspension concentrates of Linuron have been described as well, but they could not gain in importance in practice, although there is a considerable demand of flowable suspension concentrates because of their convenient handling and the fact that they are inflammable. U.S. Pat. No. 3,060,084 claims suspension concentrates containing polycarboxylated hydrocarbon polymers, for example salts of polyacrylic acids. An example with Linuron is not given, but it is stated in the specification that Linuron could be formulated in similar manner. If, however, Linuron is formulated with the suspension auxiliaries indicated in said specification or with other known dispersing agents and wetting agents to give the desired suspension concentrates, the products become more and more unstable with prolonged storage at temperatures of up to 50° C. The dispersions become thick or even solid and sediments of active substance that cannot be dispersed again are formed (cf. comparative Examples 1 and 2).

Comparing the particle distribution of a freshly prepared dispersion with that of samples stored, for example, for 2 or 3 months at 50° C., it is found that in a suspension concentrate of Linuron having good flow properties just after preparation a recrystallization to coarse Linuron crystals at the expense of the fine ones takes place during storage because of the given minor water solubility of the active substance of 80 ppm at 20° C. The crystal growth can be demonstrated, for example, by microphotography. This crystal growth of Linuron is the main reason for the instability of aqueous Linuron dispersions since in this manner the total surface of the Linuron particles, the particle number and their size continuously change, whereas the amount and type of dispersing agent and wetting agent had to be carefully selected with respect to the requirements, the initial amount of particles and particle surface in order to obtain higher concentrated active substance suspensions capable of being poured.

Therefore, aqueous dispersions containing from 20 to 50% by weight of Linuron in a particle fineness of about 5 microns normally contain uniformly shaped crystals of a diameter of up to 70 microns and above after a storage time of 2 months at 50° C. In all these cases the active substance deposits in the suspension in the form of tough and sometimes even solid sediments or the preparations solidify to cuttable pastes.

Surprisingly, it has now been found that all the aforesaid disadvantages in connection with the crystallization of Linuron from aqueous concentrates or from aqueous dilutions of liquid concentrates can be overcome and the crystal growth of Linuron in such aqueous systems can be hindered by adding fat-soluble disazo dyes to the liquid, emulsifiable concentrates or to the aqueous suspension concentrates containing Linuron as herbicide.

It is, therefore, the object of the present invention to provide liquid compositions containing Linuron as herbicide in the form of emulsifiable concentrates or aqueous suspension concentrates, which compositions additionally contain fat-soluble disazo dyes inhibiting the crystallization of the active substance in aqueous emulsions of the emulsifiable concentrates or in aqueous suspension concentrates and the aqueous dilutions thereof.

The herbicidal compositions contain according to the invention preferably from 0.05 to 2% by weight, more preferably from 0.1 to 0.5% by weight of fat-soluble disazo dyes.

More particularly, the present invention provides liquid, emulsifiable, herbicidal concentrates containing Linuron as active substance, organic solvents and emulsifiers, which concentrates contain 10 to 25% by weight of Linuron,
25 to 40% by weight of ketones, preferably isophorone and/or cyclohexanone,
60 to 18% by weight of aromatic solvents optionally containing up to 35% by weight of saturated hydrocarbons,
0.05 to 2% by weight of fat-soluble disazo dyes and
4.95 to 15% by weight of emulsifier.

The invention also provides liquid, aqueous, herbicidal suspension concentrates containing Linuron as active substance, surface-active substances and optionally suspension auxiliaries, defoamers and antifreezing agents, which concentrates contain 20 to 50% by weight of Linuron,
2 to 20% by weight of surface-active substances,
0 to 2% by weight of suspension auxiliaries,
0 to 2% by weight of defoamers,
0.05 to 2% by weight of fat-soluble disazo dyes,
0 to 4% by weight of antifreezing agents and water as balance to 100% by weight.

Suitable fat-soluble disazo dyes to be used for inhibiting the crystal growth and stabilizing the emulsion or suspension concentrates are, for example the fat-soluble disazo dyes listed in "Colour Index, third edition, volume 4 (1971), published by the Society of Dyers and Colorists, England.

Preferred disazo dyes listed in the Colour Index are, for example,

No. 26,100 (fat-soluble red HRR)
No. 26,105 (fat-soluble red BB)
No. 26,125 (fat-soluble red 5B)
No. 26,150 (fat-soluble black HB)

(the designations in brackets being the commercial names of corresponding products of Messrs. Hoechst AG).

Mixtures of different fat-soluble disazo dyes can also be used.

The term surface-active substances is intended to include dispersing agents and wetting agents. The following surface-active compounds are named by way of example: soaps, sodium alkylbenzene-sulfonates, sodium lauryl-sulfonates, sodium butylnaphthalene-sulfonates, sodium oleoyl-N-methyl-taurides, alkali metal and ammonium lignosulfonates, sodium salts of naphthalenesulfonic acids condensed with formaldehyde, sodium salts of sulfonated phenol-formaldehyde condensates and sulfonated phenol-urea-formaldehyde condensates, fatty alcohol polyglycol ethers, fatty alcohol polyglycol ether phosphates, fatty alcohol polyglycol ether sulfates, polymerized alkylaryl and arylalkyl sulfonates.

Suitable suspension auxiliaries, which, in addition, reduce the viscosity of the dispersions are preferably swellable mineral powders, for example bentonite or montmorillonite powder.

Defoamers to be used are all foam inhibiting substances, preferably silicone defoamers such as siloxanes.

As antifreezing agents ethylene glycol, propylene glycol or glycerol may be used.

Aromatic solvents used are, for example, alkylbenzenes, preferably xylene, as well as higher boiling industrial grade distillates of aromatic compounds, for example on the basis of mineral oil, boiling in the range of from 156° to 312° C. (at atmospheric pressure). The aromatic distillates may contain up to about 35% by weight of saturated paraffinic or alicyclic hydrocarbons.

Suitable ketones are preferably aliphatic or cycloaliphatic ketones, especially liquid ketones the flash point of which (measured in a closed vessel) is above 40° C. The ketones are used to improve the solubility of Linuron in aromatic solvents and to improve the stability in the cold of the emulsifiable Linuron concentrates, for example down to a temperature of about 0° to −10° C. Especially good results are obtained with isophorone and cyclohexanone and more especially isophorone.

An especially preferred solvent combination is that of isophorone with xylene.

Emulsifiable concentrates are obtained, for example, by dissolving the active substance in organic solvents or solvent mixtures, for example xylene and isophorone, with addition of emulsifiers and optionally further formulation auxiliaries.

Emulsifiers are intended to include all known surface-active compounds used as auxiliaries for the formulation of emulsifiable concentrates and soluble in xylene, for example calcium salts of dodecylbenzene sulfonic acids or calcium salts of chlorinated $C_{13}$–$C_{15}$-alkane sulfonic acids, besides polyglycol ethers, for example of nonyl phenols or triisobutyl phenols, or polyglycol ethers of fatty alcohols or reaction products of castor oil with ethylene oxide.

To prepare the suspension concentrates of Linuron according to the invention the Linuron can be stirred in the aqueous solution of the surface-active substance in which the fat-soluble disazo dye and the suspension auxiliary are suspended, the dispersion obtained can then be preliminarily comminuted to a fineness of about 200 to 300 microns in a tooth disk mill or corundum disk mill and finally finely milled in a friction ball mill with water-cooled jacket to a fineness of about 5 microns.

The emulsifiable concentrates of Linuron can be prepared in simple manner, for example by adding Linuron, emulsifiers and the fat-soluble disazo dye in dosed quantities to the solvents and dissolving the constituents while stirring.

For application the volume of suspension concentrates or of emulsifiable concentrates, depending on the desired concentration, is measured, stirred with water and sprayed on the field in the form of diluted suspensions, emulsions or suspo-emulsions.

The emulsifiable concentrates and aqueous suspension concentrates of Linuron stabilized according to the invention to inhibit crystallization are chemically and physically extremely stable in storage and stable as regards their utilitarian properties as could be ascertained by storage tests under severe conditions, for example for 3 months at 50° C., or by various tests in the cold.

It is surprising that when used in comparable concentrations, the concentrates of Linuron stabilized according to the invention exhibit a better herbicidal effect than wettable powders of Linuron so that by emulsifying or suspending comparable formulations in water active substance can be saved in practice.

For combating weeds herbicidally effective amounts of the concentrates according to the invention are applied to the infested areas or substrates in the form of aqueous emulsions or suspensions.

The following examples illustrate the invention. They demonstrate the effect of the dyes on the crystal growth and the biological effectiveness of Linuron concentrates formulated in accordance with the invention. In the biological examples a commercial wettable powder containing 50% by weight of Linuron is used as the comparative composition.

EXAMPLES OF FORMULATION

Comparative Example 1

In a friction ball mill an aqueous suspension concentrate composed of
40.0% by weight of Linuron,
5.0% by weight of sodium lignosulfonate (Vanisperse CB),
1.0% by weight of polymerized alkylaryl sulfonic acid in the form of its sodium salt (Darvan No. 3),
0.2% by weight of pulverulent montmorillonite,
0.5% by weight of silicone defoamer (SE$_2$, Wacker Chemie) and
53.3% by weight of water
is milled to a fineness such that 96% by weight of the particles are smaller than 5 microns, measured in a Coulter counter. For the measurement a saturated aqueous Linuron solution is preferred as diluent.

The suspension concentrate obtained has good flow properties and is easy to pour. When it is stored, it becomes more and more viscous and a sediment forms as for example when the dispersion is stored for 2 to 3 months at 50° C.

When microphotos taken with a Polaroid camera of samples of the suspension concentrate (each time 0.5 ml of concentrate diluted with 99.5 ml of water) are compared, it can be seen that, in contradistinction to the freshly prepared concentrate, in the stored product the preponderant portion of fine particles of active substance has been changed by recrystallization to coarse Linuron crystals of the typical cone form having a diameter of up to 70 microns.

Comparative Example 2

(Corresponding to Example 2 of U.S. Pat. No. 3,060,084)

Under the conditions of comparative Example 1, a Linuron dispersion is prepared from
42.50% by weight of Linuron,
3.00% by weight of surface-active substance (Atlox 8916 P)
0.25% by weight of suspension auxiliary (Carbopol 934)
0.70% by weight of 10% sodium hydroxide solution,
0.20% by weight of silicone defoamer (SE2) and
53.35% by weight of water.

During storage for 2 to 3 months at 50° C. the dispersion solidifies to a cuttable paste.

In the product stored for 2 to 3 months the Linuron crystals have grown to a size of 65 microns in diameter and above, compared with a particle fineness of less than 5 microns of 95% of the crystal magma in the freshly milled suspension concentrate.

Comparative Example 3

An emulsifiable Linuron concentrate is prepared from
20.0% by weight of Linuron,
30.0% by weight of isophorone,
37.0% by weight of distilled aromatic hydrocarbon compounds, boiling range 198° to 316° C. and containing 70% by weight of aromatics and 30% by weight of saturated hydrocarbons,
4.0% by weight of castor oil polyglycol ether (40 EO),
6.0% by weight of calcium dodecylbenzene sulfonate and
3.0% by weight of triisobutylphenol polyglycol ether (30 EO)
EO meaning the number of ethylene oxide units in the polyglycol ether radical.

To test the stability of an aqueous emulsion of the concentrate 2.5 ml thereof are stirred with 97.5 ml of water. First a milky, blue and opalescent emulsion is obtained which loses its opalescence after a few minutes with separation and sedimentation of Linuron crystals having a length of up to 150 microns after 15 minutes and up to 250 microns after 30 minutes.

EXAMPLE 1

In the manner described in comparative Example 1 a suspension concentrate is prepared from the same constituents but with the addition of 0.5% by weight of the disazo dye fat-soluble black HB (Colour Index No. 26,150). The suspension concentrate obtained is stable in storage and even after a storage time of over 3 months at 50° C. it keeps its particle distribution and does not change its viscosity. After the storage test the pouring and dosing properties have not changed. The concentrate has the following composition:
40.0% by weight of Linuron,
5.0% by weight of sodium lignosulfonate (Vanisperse CB),
1.0% by weight of polymerized alkylaryl sulfonic acid in the form of its sodium salt (Darvan No. 3),
0.2% by weight of pulverulent montmorillonite,
0.5% by weight of silicone defoamer (SE2),
0.5% by weight of fat-soluble black HB and
52.8% by weight of water.

EXAMPLE 2

In the suspension concentrate prepared as described in Example 1 the fat-soluble black HB is replaced by the same amount of the disazo dye fat-soluble red HRR (Colour Index No. 26,100). The dispersion obtained is stored under severe conditions for 3 months at 50° C. After that time the pouring properties are the same as directly after preparation and a minor crystal growth to particle sizes of at most 12 microns only can be observed.

EXAMPLE 3

An emulsifiable concentrate is prepared as described in comparative Example 3, but with the addition of 0.1% by weight of the disazo dye fat-soluble red BB (Colour Index No. 26,105) or 0.1% by weight of fat-soluble red HRR (Colour Index No. 26,100). In the emulsion in water the stability test shows that with retardation and after about 30 minutes only part of the Linuron starts to separate in the form of fine crystals of 10 to 20 microns with formation of a suspo-emulsion. After 2 hours of crystal growing a particle size of 30 to 40 microns is not exceeded, even not in water of 10° C. in which in general crystals grow more rapidly. The particle size distribution of the Linuron dispersed in the suspo-emulsion after standing for several hours corresponds to the particle size distribution of a Linuron wettable powder. In the suspo-emulsion no sedimentation of Linuron can be observed and the preparation exhibits the same full biological effect as a freshly prepared emulsion.

BIOLOGICAL EXAMPLES

Comparative tests to determine the herbicidal effect of Linuron in the form of a 50% wettable powder, a 40% dispersion and a 20% emulsion concentrate are carried out.

Wheat (Triticum), oat (Avena) and mustard (Sinapsis) are grown in pots in loamy soil and after emergence the plants are sprayed under a spraying pressure of 3 bar with the Linuron formulations in the indicated concentrations and an amount corresponding to 300 liters per hectare. The damage in percent is examined after 4 weeks and expressed in percent, referred to untreated control plants (=0). The results are indicated in the following Table.

It can be seen that the dispersion and the emulsifiable concentrate have a slightly better effect. In the application the dispersion and the emulsifiable concentrate have the further advantage over the wettable powder that they can be measured volumetrically and need not be weighed when the spray liquor is prepared.

TABLE

| composition | dose kg/ha active substance | damage in % wheat | oat | mustard* |
|---|---|---|---|---|
| Linuron 50% | 0.06 | 0 | 0 | 94 |
| wettable powder | 0.13 | 10 | 15 | 100 |
| (commercial) | 0.25 | 46 | 48 | 100 |
| Linuron 40%. | 0.06 | 0 | 0 | 95 |
| dispersion of | 0.13 | 12 | 15 | 100 |
| Example 1 | 0.25 | 50 | 55 | 100 |
| Linuron 20% | 0.06 | 0 | 0 | 98 |
| emulsifiable | 0.13 | 16 | 17 | 100 |
| concentrate of | 0.25 | 54 | 58 | 100 |

*as representative of dicotyledonous weeds

What is claimed is:

1. A liquid herbicidal composition in the form of an emulsifiable concentrate or an aqueous suspension concentrate consisting essentially of an effective amount of Linuron as an active component in admixture with 0.05 to 2% by weight of a fat-soluble disazo dye selected from the group consisting of solvent red 23 (C.I. 26100), solvent red 24 (C.I. 26105), solvent red 27 (C.I. 26125) and solvent black 3 (C.I. 26150) wherein said disazo dye is present in an amount sufficient to inhibit the crystallization of said active component in aqueous emulsions of the emulsifiable concentrate or in aqueous suspension concentrates and the aqueous dilutions thereof.

2. The herbicidal composition of claim 1 containing 0.1 to 0.5% by weight of the fat-soluble disazo dye.

3. The liquid herbicidal composition of claim 1 in the form of an emulsifiable concentrate containing
10 to 25% by weight of Linuron,
25 to 40% by weight of ketones,
60 to 18% by weight of aromatic solvents,
0.05 to 2% by weight of fat-soluble disazo dyes, and
4.95 to 15% by weight of emulsifier.

4. The liquid herbicidal composition of claim 3 containing 0.1 to 0.5% by weight of the fat-soluble disazo dye.

5. The liquid herbicidal composition of claim 3 wherein said ketones are isophorone or cyclohexanone or both.

6. The liquid herbicidal composition of claim 3 wherein said aromatic solvent contains up to 35% by weight of saturated hydrocarbons.

7. The liquid herbicidal composition of claim 1 in the form of an aqueous suspension concentrate containing
20 to 50% by weight of Linuron,
2 to 20% by weight of surface-active substances,
0 to 2% by weight of suspension auxiliaries,
0 to 2% by weight of defoamers,
0.05 to 2% by weight of fat-soluble disazo dyes,
0 to 4% by weight of antifreezing agents and water as balance to 100% by weight.

8. The liquid herbicidal composition of claim 7 containing 0.1 to 0.5% by weight of the fat-soluble disazo dye.

9. A method for combating weeds which comprises applying to a locus of weed growth a herbicidally effective amount of a composition as claimed in any one of claims 1, 2, 3, 4, 5, 6, 7 or 8 in the form of an aqueous dilution.

* * * * *